US00PP10549P

United States Patent [19]

Bjorge et al.

[11] Patent Number: Plant 10,549

[45] Date of Patent: Aug. 11, 1998

[54] 'FA 80' PEACH TREE

[75] Inventors: Annette Bjorge; Randy Bjorge, both of Coloma, Mich.

[73] Assignee: International Plant Management, Lawrence, Mich.

[21] Appl. No.: 738,255

[22] Filed: Oct. 28, 1996

[51] Int. Cl.[6] ..... A01H 5/00

[52] U.S. Cl. ..... Plt./43.2

[58] Field of Search ..... Plt./43.2

*Primary Examiner*—James R. Feyrer

[57] ABSTRACT

A new peach, (*Prunus persica*) variety which was developed by Annette and Randy Bjorge in a breeding program at Fruit Acres Farm in Coloma, Mich., having the following combination of unique and desirable features:

1. A fruit with excellent shipping and storage qualities.
2. A fruit maturing 17 days later than the 'Redhaven' peach.
3. A substantially round fruit with clear yellow flesh and an attractive solid red blush on the most exposed surfaces which suffuses to a relatively indistinct red-on-red stripe on the less exposed surfaces covering 90 to 100% of the fruit at maturity.
4. A fruit with flesh that does not brown when it is cut.
5. A tree and fruit with good resistance to Bacterial Spot.
6. A tree and blossom with good hardiness.

3 Drawing Sheets

ORIGIN OF THE VARIETY

The new variety of peach tree, (hereinafter referred to as the 'FA 80' peach tree) was developed by Annette and Randy Bjorge in a peach breeding program at Fruit Acres Farms, 2559 Friday Road, Coloma, Mich.) 49038. The 'FA 80' peach tree was developed as a first generation cross between 'Fayette' and 'Newhaven', two established, non-patented, commercial varieties. The parent tree was grown and maintained in a peach tree breeding orchard in Fruit Acres Farms.

This new and distinct variety of peach tree has been asexually propagated by budding at Fruit Acres Farms in Coloma, Mich. The asexual propagation demonstrates that such reproduction of the characteristics of the tree are consistent and are established and transmitted through succeeding generations.

SUMMARY OF THE VARIETY

The new and distinct variety of peach tree is of medium, compact growth with medium density and is a regular and productive bearer of peaches. The fruit of the new variety is characterized by round, substantially 90% red fruits that present a very attractive appearance. The fruits have firm flesh and are resilient to the extent that they may be handled and packaged mechanically without damaging the same for shipment. This results in less spoilage and a greater market value. The flesh of the fruits of the new variety does not brown when cut. The fruits of the new variety have a recessed pistil point which avoids damage during picking and handling.

The tree and fruits of the new variety exhibit good resistance to Bacterial Spot and are very cold hardy. The fruit matures in the middle of the peach growing season in Southwestern Michigan. It ripens 17 days after the established commercial variety, 'Redhaven'.

BRIEF DESCRIPTION OF THE PHOTOGRAPHS

The accompanying photographs show typical specimens of the new variety in color as nearly true as it is reasonably possible to make the same in color illustrations of this character. The specimens were photographed in Van Buren and Berrien counties of Southwestern Michigan.

FIG. 1. illustrates specimens of the fully ripened fruit and foliage of the new variety.

FIG. 2. illustrates blooms of the new variety.

FIG. 3. Illustrates two specimens of the new variety. The upper specimen is bisected along the suture, the lower specimen is bisected as a ninety-degree angle to the plane of the suture. The color and forms of the flesh, pit and pit cavity are illustrated.

DETAILED DESCRIPTION OF THE VARIETY

Figure 1:
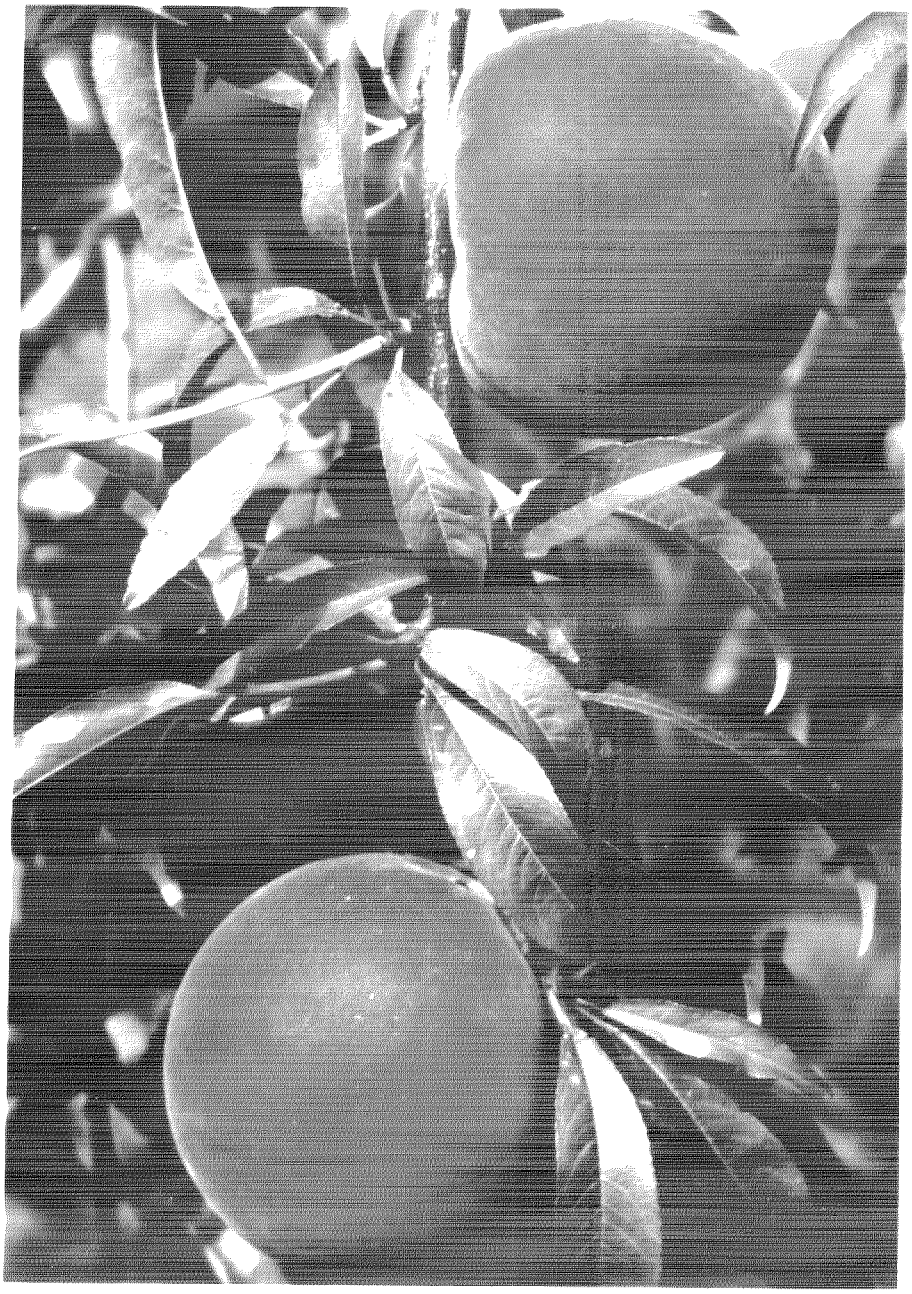
Figure 2:
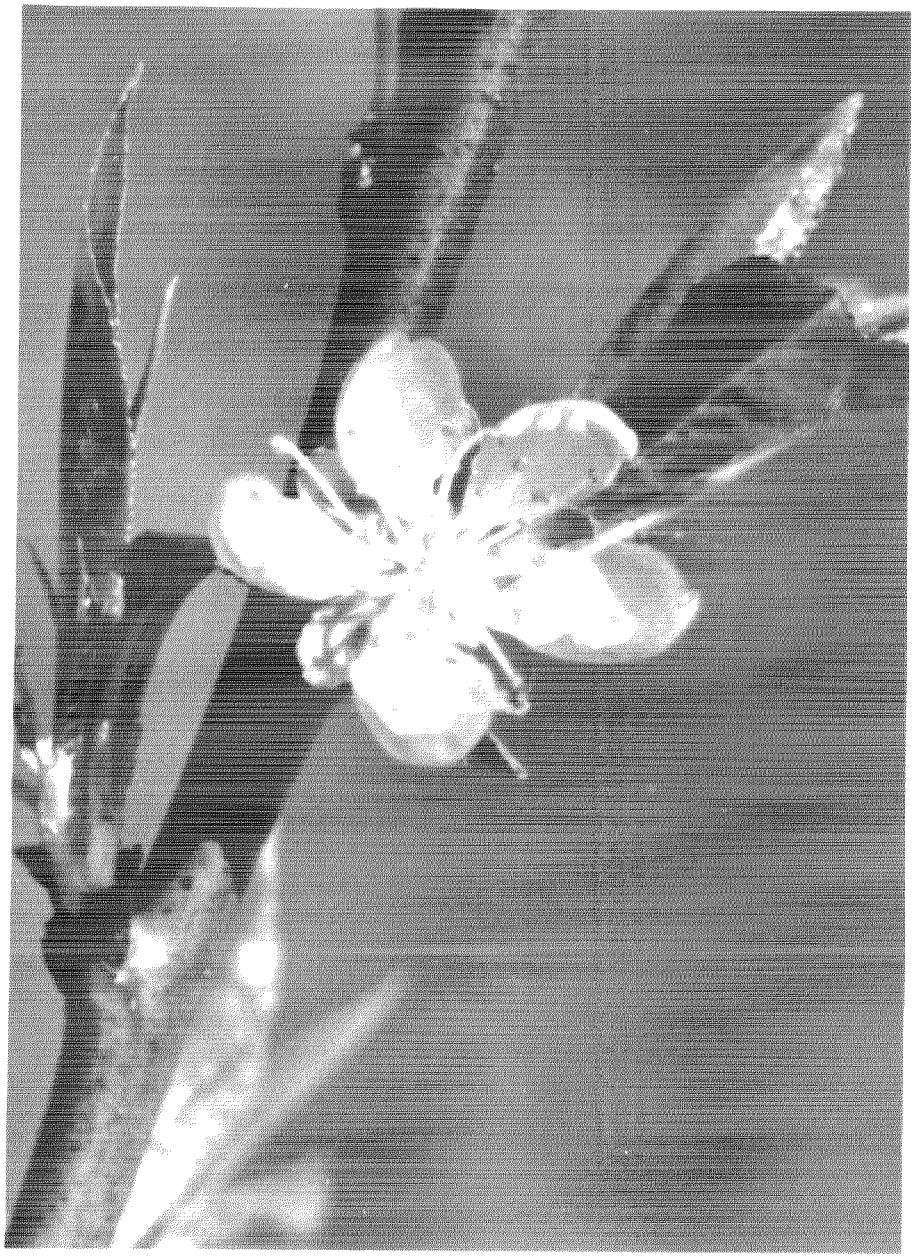
Figure 3:
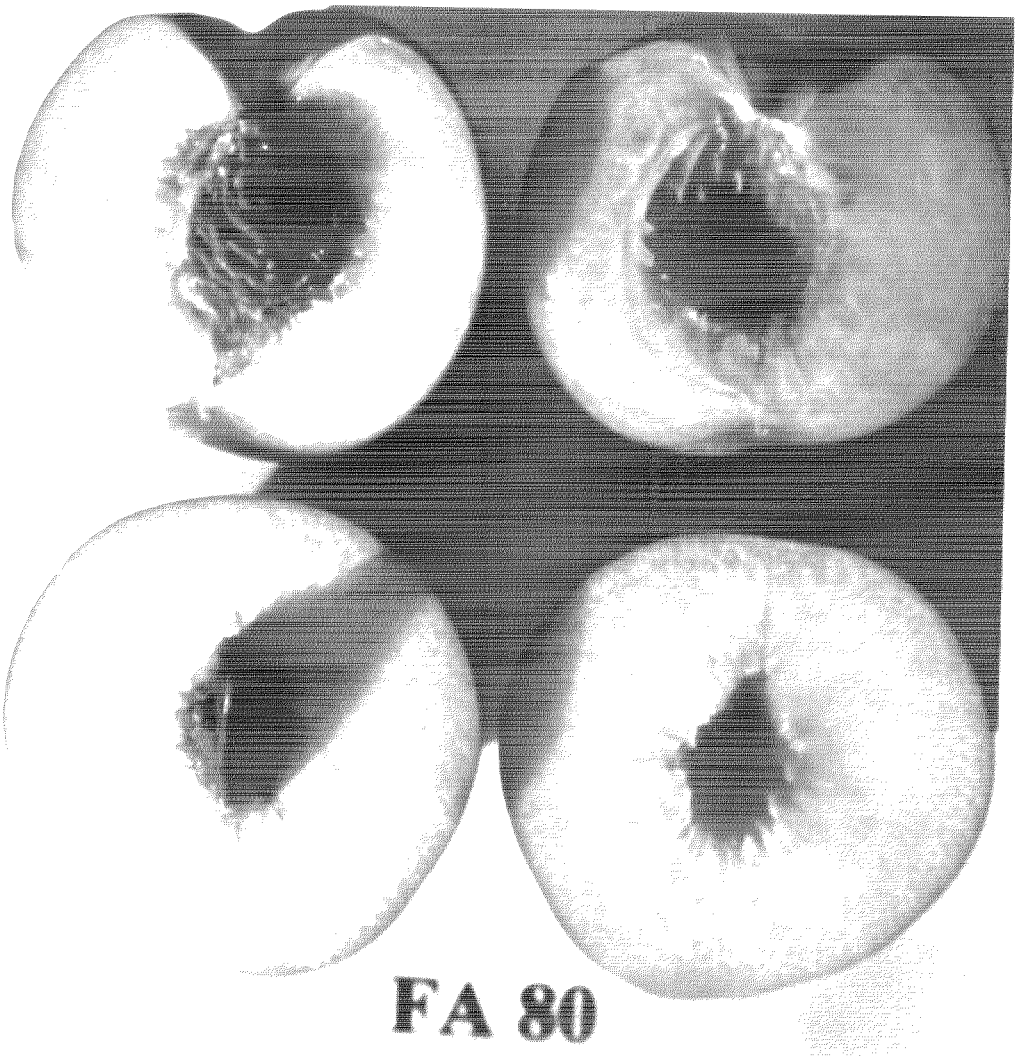

The following description of the fruit and foliage of the new variety is based on observations of specimens grown in Berrien and Van Buren County of Southwestern Michigan. The color terminology is in accordance with The Royal Horticultural Society Colour Chart, published by The Royal Horticultural Society of London, England.

Tree:

*Age of specimen.*—15 years

*Height.*—Unpruned 4.3M.

*Width.*—Unpruned 4.6M.

*Size.*—Medium.

*Vigor.*—Very vigorous, require annual spring pruning and moderate to heavy thinning.

*Density.*—Medium, internode distances average 2 to 2 ½ cm.

*Form.*—Upright, open. Major scaffold branches for a 40° to 45° angle to the trunk. Will form a central leader if left unpruned.

*Production.*—Excellent, will ripen in 2 pickings with 70 % of the crop being mature for the first picking and 30% of the crop mature for the second picking. Is more productive than its parents, similar in productivity to 'Redhaven'.

*Bearing.*—Annual, fruits will hold on the tree for 1 week at maturity. The harvest season lasts 4 days in an average year.

*Disease resistance.*—Very resistant to bacterial spot.

*Cold hardiness.*—Very hardy.

Trunk:

*Size.*—Large.

*Surface.*—Smooth.

*Lenticils.*—Medium.

*Color.*—Gray 201 B.

Leaves:

*Size.*—Length 128 mm, width 28 mm.

*Form.*—Lanceolate — pointed.

*Thickness.*—Medium.

*Texture.*—Medium.

*Margin.*—Crenate.

*Petiole.*—Length 8 to 10 mm, 1 mm thick.

*Glands.*—Round, number varies from 3 to 5, average 3. Located on base of leaf and upper portion of petiole.

*Color.*—Upper surface Green 147 A, lower surface Green 147 B.

*Stipules.*—None.

Flower buds:

*Size.*—Medium.

Flowers:

*Blooming period.*—April 8 to 15 in Coloma, Mich.

*Presentation.*—Medium showy.

*Pollen.*—Present, self-fertilizing.

*Petals.*—5 in number, cupped inward, slightly folded longitudinally, Red-Purple 73A.

*Stamens.*—Length 10 to 11 mm, White 155 A.

*Pistil.*—15 mm.

Fruit:

*Maturity when described.*—Firm ripe.

*Date of first picking.*—August 18, in Coloma, Mich.

*Size.*—65 to 80 mm.

*From.*—Round

*Suture.*—Inconspicuous.

*Pistil point.*—Inverted.

Skin:

*Thickness.*—Medium

*Texture.*—Fine

*Tendency to crack.*—None.

*Down.*—slight.

*Color.*—90 to 100% Red 46 A blush on most of the exposed surfaces which suffuses to a blush Red 45 B over a background of Yellow-Orange 19 A. Some indistinct red on red striping on the less exposed surfaces.

Flesh:

*Texture.*—Fine, firm.

*Aroma.*—Medium.

*Fibres.*—Small, few, tender, not conspicuous or noticeable in eating.

*Color.*—Yellow-Orange 22 A., some Red 43 C around the pit.

*Eating quality.*—Very high with medium sweetness and medium acid.

*Coloration at the pit.*—Red bleeding into the flesh around 60 to 80 % of the pit.

Stone:

*Size.*—Length 35 mm, width 26 mm, thickness 17 mm.

*Form.*—Ovate.

*Apex.*—Pointed

*Sides.*—Nearly equal.

*Base.*—Straight to slightly slanted.

*Surface.*—Pitted to furrowed throughout.

*Color.*—Grayed-Orange 175 A.

*Type.*—Freestone.

*Tendency to crack.*—None.

Use. Desert, fresh and commercial market.

Shipping quality. Excellent.

Keeping quality. Excellent, 4 weeks in common cold storage.

Disease resistance. Excellent resistance to bacterial spot.

I claim:

1. A new and distinct variety of peach tree, *Prunus persica,* substantially as herein shown and described, characterized particularly as to novelty by the unique combination of medium, compact size, vigorous, upright, open, medium density, regular bearing tree, with good resistance to bacterial spot, producing freestone fruits having clear yellow, non-browning flesh and substantially round, firm, 90% blushed red skin color at maturity which occurs 17 days after the maturity of 'Redhaven' peach.

* * * * *

FA 80